United States Patent [19]

Mastel

[11] Patent Number: 5,312,393
[45] Date of Patent: May 17, 1994

[54] RING LIGHTING SYSTEM FOR MICROSURGERY

[76] Inventor: Douglas Mastel, 2843 Sanco Rd., Ste. V, Rapid City, S. Dak. 57702-9368

[21] Appl. No.: 999,151
[22] Filed: Dec. 31, 1992
[51] Int. Cl.⁵ ............................................. A61B 17/36
[52] U.S. Cl. ........................................... 606/4; 606/6; 606/10; 359/385
[58] Field of Search ................. 606/4, 10, 11, 6; 128/395; 359/385, 387, 389, 390; 362/216, 253, 32

[56] References Cited

U.S. PATENT DOCUMENTS

| | | | |
|---|---|---|---|
| 3,796,220 | 3/1974 | Bredemeier | 606/18 |
| 4,527,870 | 7/1985 | Esmay | 359/389 |
| 4,719,912 | 1/1988 | Weinberg | 606/4 |
| 4,887,892 | 12/1989 | Bacus | 359/385 |
| 4,898,439 | 2/1990 | Mori | 606/16 |

FOREIGN PATENT DOCUMENTS

0191114  8/1988  Japan ..................... 359/385

*Primary Examiner*—Stephen C. Pellegrino
*Assistant Examiner*—Sonya Harris
*Attorney, Agent, or Firm*—Frank D. Gilliam

[57] ABSTRACT

A system for lighting a field for diagnosis or microsurgery, especially eye surgery. Basically, in one embodiment a ring light having a diameter sufficient to surround the objective lens of a surgical microscope is mounted on a housing adjacent to the objective lens. The ring light provides broad, shadowless illumination over the surgical site. In addition, where surgery of the cornea is to be undertaken, a ring of light is reflected from the cornea surface and can be observed through the microscope as indicative of astigmatism. In alternate embodiment, two smaller ring lights are mounted on the housing surrounding and coaxial with the microscope entrance pupils. In this case two circular rings in a figure eight configuration are projected onto the cornea. A light intensity varying mechanism controls ring light intensity. A center light is provided between the objective lenses providing a point source for uniformly illuminating the central portion of the microsurgery site. Preferably, the center light is a fiber optic light source. A separate intensity controlling mechanism is provided for the center light, so that the intensity of each light can be independently varied, as desired. This lighting arrangement provides much less glare in the eyes of the surgeon and lower intensity and greater comfort for the eye of a patient.

14 Claims, 2 Drawing Sheets

RING LIGHTING SYSTEM FOR MICROSURGERY

BACKGROUND OF THE INVENTION

This invention relates in general to devices for illuminating the site of microsurgery, in particular eye surgery, and, more specifically, to a microsurgery ring illumination system.

Conventional surgical microscopes are stereoscopic, having a large objective lens oriented adjacent to the microsurgery site. Entrance pupils are spaced across the objective lens to collect a stereo image off the single, large diameter, long working distance objective lens. Powerful and bright illumination systems are provided to illuminate the surgical field. Some use an oblique system, where the light source is adjacent to the objective lens housing and is angled at the surgical field. Others mount the light adjacent to, and somewhat coaxial with, the entrance pupils. Typically they are powered with a halogen light bulb, sometimes with a fiber optic system conveying light from a remote source.

These illumination systems have a number of drawbacks. Shadows are created if a hand or instrument blocks the light path, often obscuring critical areas of the surgical field. The lighting is non-uniform due to the essentially single point light source at an angle to the microscope optical pathways, resulting in overly bright light on the source side, falling off to insufficient light on the other side. Even more significantly, glare from reflections off instruments or devices (or even tissue and fluids) inhibit the surgeons visualization and can adversely affect surgical efficiency. These problems are of particular importance in eye surgery where seeing transparent membranes is critical. Due to poor light delivery, surgeons are forced to turn the lights to near maximum levels to see the internal structures in, for example, cataract surgery. By doing so, however, they greatly increase surface glare from the fluids at the surface of the eye, seriously degrading their sight. This combination of overly bright lights and glare is uniformly disliked by surgeons and may be damaging to the sight of the surgeons getting such large lumen doses in his/her eyes.

A coaxial light source, from the patient's perspective, is much like looking into the sun. It has long been established that harm is done to retinas during eye surgery due to the light conditions. Retinal damage may manifest as light sensitivity, or photophobia, photic maculopathy (transient partial vision loss) due to exposure to intense light and sometimes cystoid macular edema (CME) which is essentially hardening of the arteries in the eye. CME is particularly devastating because it destroys the function of the most central vision and highest acuity of the macula. In essence, the high light level burns the retina.

Commonly, about a 2% CME rate is attributed to cataract surgery, although other factors in addition to high light intensity such as posterior capsule rupture can contribute to CME. Some studies indicate that angiographic postoperative CME of up to 25-30% can occur. This may manifest as subclinical losses in contrast sensitivity, color loss, etc.

In many types of eye surgery the eye is not injected with an anesthetic to deaden the eye. Some eye surgeries such as radial keratotomy, pterygium removal and certain new cataract techniques are performed under topical anesthesia, leaving the patient with normal ocular function during surgery. Often, these patients cannot tolerate the high intensity prior art microscope lights.

Thus, there is a continuing need for improved systems for lighting the site of microsurgery, in particular for eye surgery which use much lower and more uniform light intensities, reduce or eliminate shadows on the surgery field from instruments or the like, greatly reduce glare from instruments and surface fluids, reduce high intensity light damage to the surgeons's eyes and, in the case of eye surgery, reduce or eliminate light damage to the patient's eye. In addition, the light pattern would desirably aid in surgical and diagnostic procedures, such as those using conventional slit-lamps.

SUMMARY OF THE INVENTION

The above-noted problems, and others, are overcome by the lighting system of this invention which preferably includes a single, toroidal, variable intensity ring light adapted to surround the objective lens or two ring lights around the entrance pupils of a conventional microscope of the sort used in microsurgery and diagnosis of eye problems. The light produced is uniform and shadow-free across the surgery field and permits use of much lower intensity light since most light is refracted and reflected back into the microscope objective lens. Further, the single ring light projects a bright circle of light and the pair of ring lights project a bright figure eight onto the cornea in eye surgery, allowing qualitative intraoperative keratoscopy for judging corneal astigmatism. In eye surgery, the patient's iris constricts and protects the retina, making the operation safer and more comfortable for the patient.

If desired, multiple small ring lights may be employed on the large diameter ring surrounding the objective lens in order to cover the cornea with multiple contour mires to essentially "map" the corneal surface topography. This in turn can be accessed by computerized mapping equipment to provide real-time intraoperative quantitative keratoscopy. Thus, astigmatism and possibly other anomalies can be quantified during surgery, allowing the surgeon to make surgical adjustments or refinements during the procedure, providing greater accuracy. Also, intermittent portions of some of the various ring lights may be covered or the ring lights could be formed as a circular series of light points, so that the pattern on the eye is "dotted". Where there are a number of ring lights, the differing pattern of continuous and interrupted reflected circles will help to prevent confusion.

Any suitable source of a ring of light may be used. Typical ring lights include ring-shaped halogen lights, fluorescent lights, and ring shaped polished cavities into which light is directed through a fiber optic bundle. Of these, the fiber optic bundle approach is preferred because it provides superior illumination.

For optimum results, a center light, in essence a point light, is provided at about the center of the ring light, typically between the objective lenses of the microsurgery microscope. The combination of large ring light and center point light is referred to as a "fixating keratoscope". The center light has adjustable intensity to provide safe, controlled, fundus lighting with an optimum angle of attack. The center light illuminates the retina for red-reflex, which is very advantageous for cataract surgery. Such a center light is often used as a patient alignment device in a number of corneal procedures as a "fixation point". The ring light or ring light combination and center light do not interfere with the existing illumination system on most microscopes and can serve adjunctly.

Any suitable light source may be used for the center light. Typical point sources include light emitting diodes, fiber optic bundles to bring light from an outside source, emitting it at the central location towards the surgery field. A centrally located light emitting diode may be used for simple centration purposes, while a fiber optic center light is optimum for use where a red-reflex is desired. Conventional optical lenses may be used to concentrate and direct light from the source towards the surgery field. For optimum results, a halogen light source is preferred for use with the fiber optic bundle.

BRIEF DESCRIPTION OF THE DRAWING

Details of the invention, and of certain preferred embodiments thereof, will be further understood upon reference to the drawing, wherein.

DETAILED DESCRIPTION OF PREFERRED EMBODIMENTS

Figure 1:
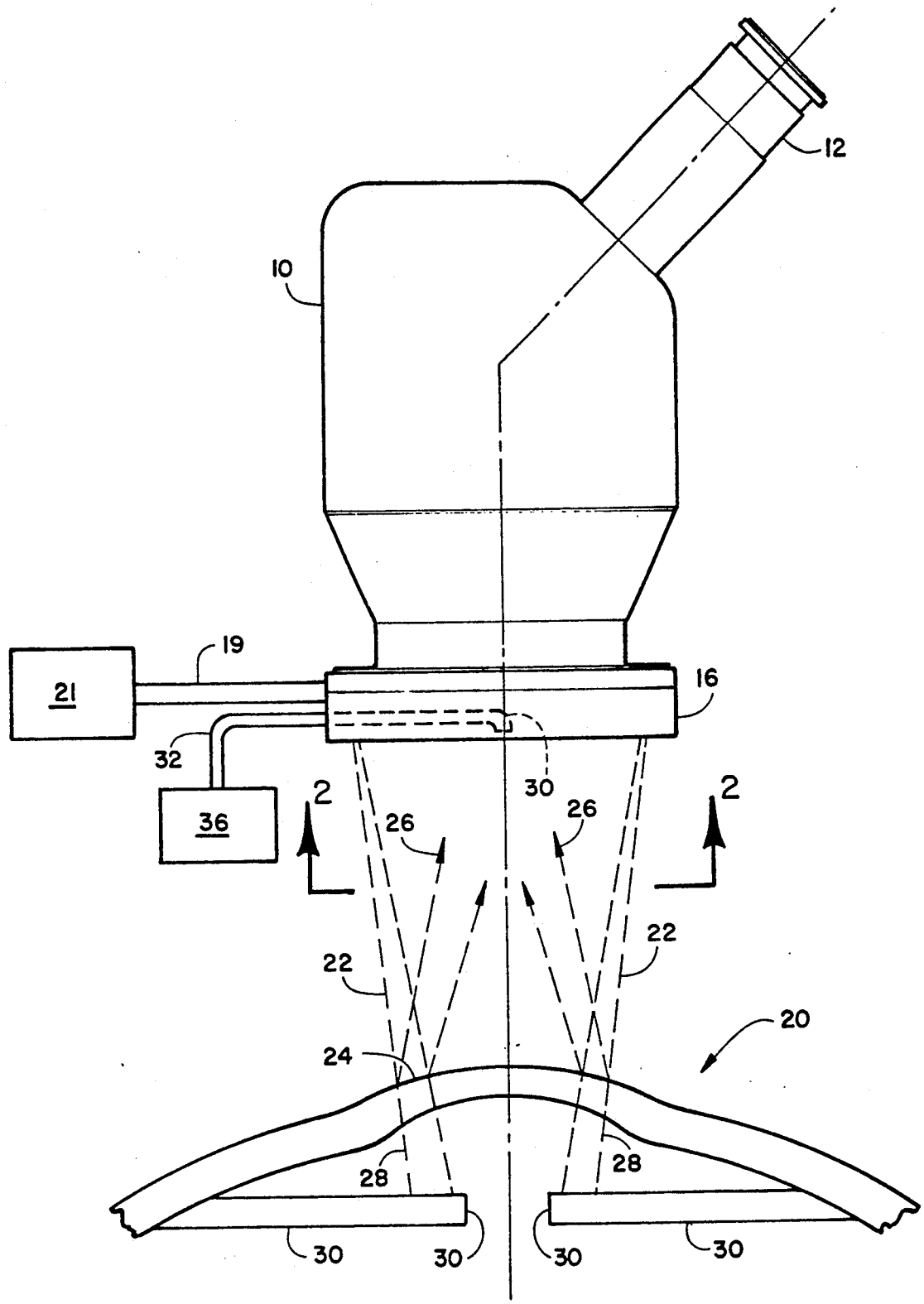
FIG. 1 is a schematic elevation view showing the lighting system of this invention juxtaposed with a microsurgery microscope and the surface of an eye.
Figure 2:
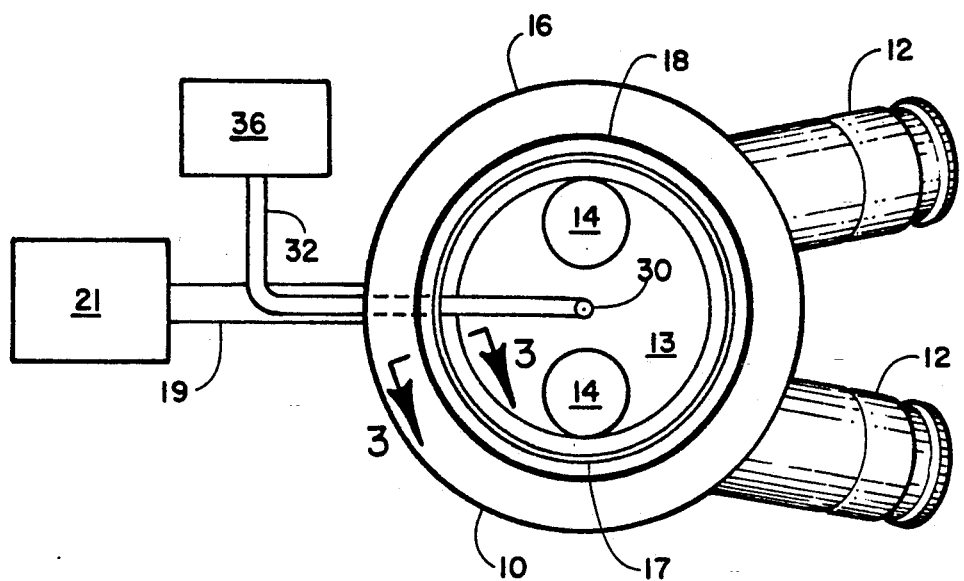
FIG. 2 is a schematic, upwardly-directed, view taken on line 2—2 in FIG. 1.

Referring now to FIGS. 1 and 2, there is seen a conventional stereoscopic microscope 10 of the sort used in diagnosis of eye problems and in microsurgery, having a pair of eyepieces 12 (only the nearest being seen), a single, large diameter, long working distance, objective lens 13 and a pair of entrance pupils 14 (seen in FIG. 2). The entrance pupils 14 are mounted above objective lens 13 and are in the nature of prisms that direct light toward eyepieces 12. Entrance pupils 14 are internally mounted separate from objective lens 13, either on a zoom pod for infinite magnification settings or on a rotary manual magnification changer, usually changing magnification over 3 or 5 steps.

A ring-shaped housing 16 is positioned around the ends of objective lens 13 on the microscope, secured in place by any conventional means, such as setscrews, threads, a bayonet mount, tight slip fit or the like. A ring shaped light source 18 is positioned on housing 16 with light from the source directed toward the eye 20 (or other field or subject of microsurgery). As mentioned above, any suitable ring-shaped light source may be used. The light source may, for example, be an annular halogen light bulb or the like exposed along its lower edge to direct light from the bulb toward the eye or other field, or the light may pass through an annular slit 17 in housing 16 below the bulb, see FIG. 3, as desired.

Light from source 18 substantially uniformly illuminates the surface of cornea 22. Power for light source 18 enters through cable 19 from power supply 21. Where cable 19 is a fiber optic bundle, power supply 21 will be a light emitter, such as a halogen bulb. From the point of view of objective 13, a circle of light is reflected back into objective 13 along a circular line 24, as indicated by light rays 26 in FIG. 1, the apparent diameter of circle 24 being determined by the microscope power and focusing distance, along with incident angle of the light source.

Figure 3:
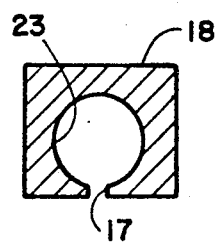
FIG. 3 is a detail section view through the ring light, taken on line 3—3 in FIG. 2.

In a preferred embodiment, the fiber optic bundle runs through an annular channel 23 having a generally circular cross section, as seen in FIG. 3. Light from the fiber optic bundle passes through slit 17 toward the eye or other field. Portions of the bundle of fibers can be gradually separated from the bundle and turned about 90° toward slit 17. This results in a row of fiber ends along slit 17, pointed towards the field. The ends of the fibers are polished to provide optimum light emission. In another arrangement, the fiber bundle can be split into two portions, one of which extends in each direction from the point along the ring at which the fiber optic bundle 19 enters. The bundle is tapered along each half at a shallow angle, with the tapered side oriented toward slit 17. The tapered portion is polished, so that light is emitted by the fibers gradually and uniformly along each tapered portion, so as to uniformly pass through slit 17 towards the field.

In another preferred embodiment, the annular, generally circular cross section channel 23 (as seen in FIG. 3) which, in this case, is a hollow polished channel having a slit 17 along the lower edge. Light enters through a fiber optic bundle 19, which terminates in channel 23. Light exits the fiber optic bundle and bounces along channel 23, a portion eventually uniformly exiting through slit 17 toward the eye.

Some of the incident light passes through the cornea, as indicated by rays 28. Since the patient's iris 30 is free to respond to the incident light, the iris 30 will naturally and automatically close down to prevent excess light passing through to the retina (not seen), unless a pupillary block is employed.

As described above, for optimum system performance, a center light source 30 is provided at the center of ring light source 18. In the preferred embodiment illustrated, light source 30 may be the end of a fiber optic bundle or a light emitting diode mounted on the end of a power cable 32. In the case of a fiber optic, power cable 32 is fiber optic cable 32 extending to a conventional external light source schematically represented at 36. With a light emitting diode, power cable is an electrical wire running from an electrical power source at 36. Any suitable condensing or diffusing lens or the like (not shown) could be used at center light source 30 to direct light in a selected direction and pattern.

The light intensity of each of ring light 18 and center light 30 is controlled by conventional means, such as potentiometers or electronic and mechanical dimmer devices, along cables 19 and 32.

In some applications, such as cataract surgery, the single ring light surrounding the entire objective lens 13 may not be optimum. Due to the convergence angle to the eye relative to the optical pathways, the surgeon may see multiple reflections inside the eye, known as "Purkinje images". These images result from reflections off the cornea's front and back surfaces and also the clear crystalline lens's front and back surfaces.

Figure 4:
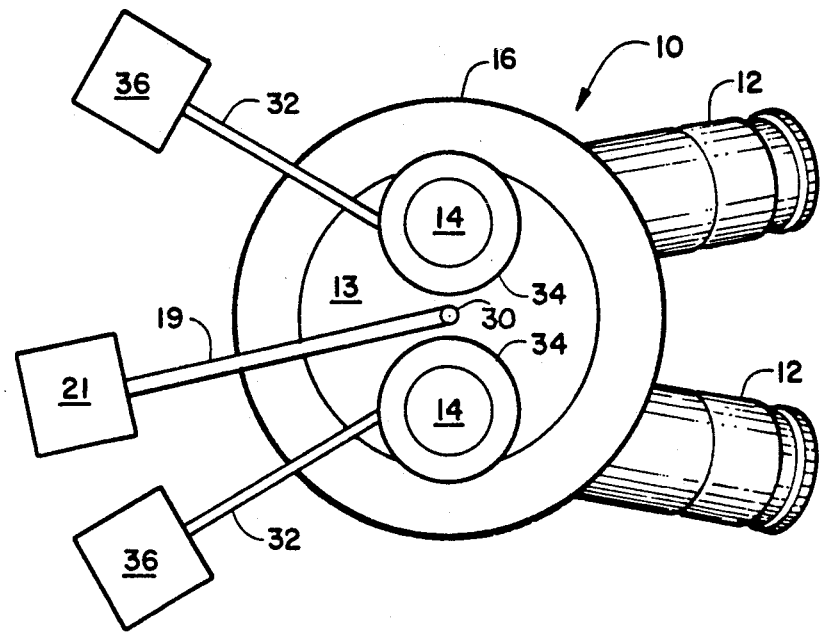
FIG. 4 is a schematic view corresponding to that of FIG. 2, showing and alternative, two-ring light, system with a large ring light.

The embodiment shown in FIG. 4 is preferred for those instances where these problems arise. The microscope 10 is basically the same as that shown in FIGS. 1 and 2, with eyepieces 12, a large objective lens 13, entrance pupils 14 and a housing 16 surrounding objective lens 13 and secured to the microscope. In this case, two small ring lights 34 are mounted on housing 16, each aligned with one entrance pupil 14. Each ring light 34 can be configured in the same manner as the large ring light described above, only on a smaller scale. A center light 30, powered through cable 19 (typically a fiber optic cable or an electrical cable to a light emitting diode). Two power supplies 36 transmit light to ring lights 34 through fiber optic cables 32 (or electrical cables in the ring lights are powered by an electrical light or the like). Of course, a single power supply 36 could be used, supplying power through a bifurcated cable corresponding to cable 32.

With the dual ring lights, the surgeon will see a figure eight reflected from the eye. This embodiment eliminates multiple Purkinje images in cases where they are a problem, provides a good red-reflex as well as the advantage that the circles of light projected onto the cornea cannot focus into a hot spot on the retina, preventing the serious problems detailed above.

While the embodiments of FIGS. 1 and 2 and of FIG. 4 are illustrated separately for clarity, both a single large ring light and the two small ring lights could be mounted on a single housing 16, with a conventional two-way light switch permitting either embodiment (or both) to be selected, depending on the diagnostic technique or surgery being performed.

Since the light sources here are normally positioned outside the microscope optical system, any desired colorizing, polarizing or other filters may be easily placed over the light sources. For example, blue filters may be used to enhance reds. Crossed polarizing filters could also be used as a manual rheostat by the surgeon Other applications, variations and ramifications of this invention will occur to those skilled in the art upon reading this disclosure. Those are intended to be included within the scope of this invention, as defined in the appended claims.

I claim:

1. A lighting system for use in microsurgery which comprises:
    a toroidal housing adapted to be fastened to a microscope having an objective lens, said housing surrounding the microscope objective lens;
    at least one ring shaped light source mounted on said housing and adapted to direct light away in one direction from the plane in which said toroidal housing lies;
    means for controlling intensity of illumination produced by said ring shaped light source;
    a center light source positioned at approximately the center of said ring shaped light source and adapted direct light away from the plane of said housing in said one direction; and
    means for controlling intensity of illumination produced by said center light source.

2. The lighting system according to claim 1 wherein said ring shaped light source comprises a single ring shaped light surrounding said objective lens.

3. The lighting system according to claim 1 wherein said ring shaped light source comprises two small ring shaped lights each surrounding one entrance pupil of said microscope.

4. The lighting system according to claim 1 wherein said center light source is a fiber optic bundle conveying light from an external source and emitting light at said center.

5. The lighting system according to claim 1 wherein said center light source is a light emitting diode.

6. The lighting system according to claim 1 wherein said center light source is a light transmitting fiber optic bundle.

7. A microscope system having a self-contained illumination system which comprises:
    a microscope including a single, large diameter, long working distance, objective lens and two spaced entrance pupils for directing light to two eyepieces;
    said objective lens adapted to be positioned adjacent to a field for observation of the field during performance of activities relating to objects in the field;
    a housing surrounding said objective lens;
    a single ring light having a center being mounted on said housing substantially co-axial with said objective lens to substantially uniformly illuminate said field;
    means for controlling light intensity of said ring light illumination; and
    a center light source positioned approximately at the center of said ring light and oriented to direct light toward the center of said field.

8. The microscope system according to claim 7, further including a center light source positioned between said entrance pupils approximately at the center of said ring light and adapted to direct light toward the center of said microsurgery field.

9. The microscope system according to claim 7 wherein said field includes the cornea of an eye and said ring light projects a bright ring on the cornea observable through said microscope.

10. The microscope system according to claim 7 wherein said ring shaped light source comprises a fiber optic bundle directing light into a toroidal channel having a slit adapted to direct light toward said field.

11. A microscope system having a self-contained illumination system which comprises:
    a microscope including a single, large diameter, long working distance, objective lens and two spaced entrance pupils for directing light to two eyepieces;
    a housing surrounding said objective lens;
    a dual ring light system consisting of two smaller diameter spaced ring lights each surrounding and coaxial with one of said entrance pupils to illuminate an adjacent field; and
    a center light source positioned between said spaced ring lights and oriented to direct light toward the center of said adjacent field.

12. The microscope system according to claim 12 wherein said center light source is a fiber optic bundle conveying light from an external source and emitting light at said center position.

13. The microscope system according to claim 12 further including means for selectively varying the intensity of the ring light system and the center light source.

14. The microscope system according to claim 12 wherein said ring shaped light source comprises a fiber optic bundle directing light into a toroidal channel having a slit adapted to direct light toward said field.

* * * * *